United States Patent [19]
Dandliker et al.

[11] Patent Number: 5,707,813
[45] Date of Patent: Jan. 13, 1998

[54] NUCLEIC ACID PROBES AND METHODS

[75] Inventors: Walter B. Dandliker, La Jolla; Robert F. Devlin, San Diego, both of Calif.

[73] Assignee: Diatron Corporation, San Diego, Calif.

[21] Appl. No.: 709,285

[22] Filed: Sep. 6, 1996

Related U.S. Application Data

[60] Division of Ser. No. 51,446, Apr. 21, 1993, Pat. No. 5,606,045, and a continuation-in-part of Ser. No. 701,465, May 15, 1991, abandoned, said Ser. No. 51,446, is a continuation-in-part of Ser. No. 701,449, May 15, 1991, Pat. No. 5,403,928, which is a continuation-in-part of Ser. No. 523,601, May 15, 1990, abandoned, said Ser. No. 701,465, is a continuation-in-part of Ser. No. 524,212, May 15, 1990, abandoned.

[51] Int. Cl.$^6$ .................. C12Q 1/68; C12P 19/34
[52] U.S. Cl. .................................. 435/6; 435/91.2
[58] Field of Search .................. 435/5, 6, 91.2; 935/77, 78

[56] References Cited

U.S. PATENT DOCUMENTS

| | | | |
|---|---|---|---|
| 5,403,928 | 4/1995 | Dandliker et al. | 540/128 |
| 5,606,045 | 2/1997 | Dandliker et al. | 536/25.32 |

*Primary Examiner*—Eggerton A. Campbell
*Attorney, Agent, or Firm*—Lyon & Lyon LLP

[57] ABSTRACT

The present invention is directed to compositions comprising an oligonucleotide linked to a detectably labeled marker component comprising a fluorophore moiety which comprises a substantially planar, multidentate macrocyclic ligand coordinated to a central atom capable of coordinating with two axial ligands and two polyoxyhydrocarbyl moieties which are attached as axial ligands to the central atom. The present invention is also directed to nucleic acid hybridization and amplification methods employing such compositions.

18 Claims, 7 Drawing Sheets

NUCLEIC ACID PROBES AND METHODS

This is a division of application Ser. No. 08/051,446, filed Apr. 21, 1993 U.S. Pat. No. 5,606,045 hereby incorporated by reference in its totality (including drawings), which is a continuation-in-part of U.S. application Ser. No. 701,449, filed May 15, 1991 U.S. Pat. No. 5,403,928, which is a continuation-in-part of U.S. application Ser. No. 523,601, filed May 15, 1990 abandoned. This application is also a continuation-in-part of U.S. application Ser. No. 701,465, filed May 15, 1991 abandoned, which is a continuation-in-part of application Ser. No. 524,212, filed May 15, 1990 abandoned.

FIELD OF THE INVENTION

The present invention relates to labeled oligonucleotides specific for some complimentary sequence of a nucleic acid, i.e., nucleic acid probes. The present invention also relates to the use of these nucleic acid probes in hybridization assays for the detection or quantification of nucleic acids in a sample in small amounts, as well as the use of these nucleic acid probes in nucleic acid amplification systems.

BACKGROUND OF THE INVENTION

Publications and other reference materials referred to herein are incorporated herein in their entireties by this reference.

Nucleic acid hybridization assays have emerged as an important method for the clinical detection of viral and microbial pathogens and genetic disorders. Assay formats are predominantly based on heterogeneous hybridization in which the target nucleic acid is sequestered on a solid support to allow separation of hybridized and unhybridized detection probe (Matthews and Kricka, *Anal. Biochem.* 169:1–25 (1988)). While these formats display good sensitivity, the necessity of separation and wash steps makes such assays time-consuming and also makes automation difficult.

Thus, presently available heterogeneous methods for detecting or quantitating nucleic acid sequences by hybridization generally involve a large number of steps and are laborious to perform. Typically, a DNA sequence to be assayed is denatured and bound to a solid support and then incubated with a probe complementary to the target nucleic acid (or a portion thereof). The probe is labeled with, for example, a radioactive label, a chemiluminescent label or an enzyme, such as alkaline phosphatase. After incubation and washing of the solid phase, it is then normally developed to give a signal, for example, in the case of a radioactive label, by autoradiography.

Sandwich-type assays are also used, in which a so-called "capture" nucleic acid probe having a sequence complementary to the target sequence is bound to a solid support, and then allowed to hybridize to the target sequence. A labeled probe is then allowed to hybridize to another portion of the target sequence. After washing, the label is detected. A "sandwich" may also be formed in solution with two probes, one containing a label and the other containing one half of an affinity pair. After hybridization, the solution is contacted with a solid phase to which the other half of the affinity pair is bound. After washing, the signal of the label is detected. For descriptions of various hybridization methods, see, for example, Hames and Higgins, eds., *Hybridization*, IRL Press (1985) and Matthews and Kricka, supra.

More recently, a number of homogeneous hybridization assays have been reported which exploit the properties of donor and acceptor fluorophor-labeled oligonucleotides to transfer or quench fluorescence energy when hybridized to an analyte (Morrison et al., *Anal. Biochem.* 183:231–244 (1989); Cardullo et al., *Proc. Natl. Acad. Sci. USA* 85:8790–8794 (1988)). Arnold et al., *Clin. Chem.* 35:1588–1594 (1989), have described a chemiluminescence-based detection assay which exploits the differential rates of hydrolysis of acridinium ester-labeled oligonucleotide probes. While sensitivities in the attomole range are reported, their assay formats require the addition of reagents to trigger the chemiluminescent reactions.

Homogeneous assays permit the monitoring of hybridization reactions in real time. However, homogeneous assays which use conventional fluorophors, such as fluorescein, are compromised by background fluorescence from biological test samples. Real time methods enable the measurement of the reaction kinetics so that the assay conditions can be optimized to quantitate the particular amount of the oligonucleotide of interest. Thus, homogeneous assays are useful to measure, for example, viral load or bacterial load, and to monitor the course of various disease states. Real-time monitoring of hybridization procedures reduces steps involved, as well as manipulation of samples, which results in lower contamination, as well as ease in automation.

Nucleic acid amplification methods, such as polymerase chain reaction (PCR), generate nucleic acid sequences which are then assayed. Thus, nucleic acid amplification methods incorporate hybridization steps, as well.

In PCR, a pair of primers (one primary and one secondary) is employed in excess to hybridize at the outside ends of complementary strands of the target nucleic acid. The primers are each extended by a polymerase using the target nucleic acid as a template. The extension products become target sequences themselves, following dissociation from the original target strand. New primers are then hybridized and extended by a polymerase, and the cycle is repeated to increase geometrically the number of target sequence molecules. PCR is described in more detail, for example, in U.S. Pat. Nos. 4,683,195 and 4,683,202. See also, Saiki et al., *Science* 230:1350–1354 (1985); Mullis and Faloona, *Methods Enzymol.* 155:335–350 (1987); Eisenstein, *New Engl. J. Med.* 322:178–183 (1990). Modifications, adaptions and enhancements of the basic PCR protocol are numerous (See, e.g., Erlich, ed., *PCR Technology: Principles and Amplifications for DNA Amplification*, Stockton Press, New York (1989); Innis et al., *PCR Protocols: A Guide to Methods and Applications*, Academic Press, New York (1990)).

More recently, an amplification method based on cycles of oligonucleotide-targeted ligation, called ligase chain reaction (LCR), has been described (Barany, *PCR Methods and Applications* 1:5–16 (1991)). Similar to the PCR protocol, the LCR method includes thermocycling steps to permit the denaturing of newly ligated oligonucleotide duplexes so that these products can serve as templates for subsequent cycles of amplification.

Allele-specific LCR employs four oligonucleotides, two adjacent oligonucleotides which uniquely hybridize to one strand of target DNA, and a complementary set of adjacent oligonucleotides which hybridize to the opposite strand. Thermostable DNA ligase will covalently link each set, provided there is sufficient complementarity at the junction. Because the oligonucleotide products from one round may serve as substrates during the next round, the signal is amplified exponentially, analogous to PCR amplification. A single-base mismatch at the oligonucleotide junction will not be amplified, and is therefore distinguished. A second set of mutant-specific oligonucleotides is used in a separate reaction to detect the mutant allele.

An alternate amplification technique is the transcription-based amplification system (TAS). Each cycle of TAS is composed of two steps. The first step is a cDNA synthesis step that produces one copy of a double-stranded DNA template for each copy of target RNA or DNA target nucleic acid. During the course of the cDNA step, a sequence recognized by a DNA-dependent RNA polymerase is inserted into the cDNA copy of the target sequence to be amplified. The second step is the amplification of the target sequence by the transcription of the cDNA template into multiple copies of RNA. This procedure has been applied to, for example, the detection of human immunodeficiency virus type 1 (HIV-1)-infected cells (Kwoh, et al., *Proc. Natl. Acad. Sci. USA* 86:1173–1177 (1989)).

These amplification techniques are potentially useful in any situation which requires the examination of DNA. The methods have been used, for example, in research fields involving genetic analysis and other fields, such as archeology and forensic pathology. By amplifying target DNA, amplification methods can supplement or replace many standard cloning methods, such as site-specific mutagenesis, complementary and genomic DNA cloning, analysis of protein-DNA interaction, DNA and RNA sequencing, and gene therapy manipulations.

With regard to specific applications in medicine, amplification methods such as PCR are used to determine whether a given sequence of DNA exists in a particular clinical specimen. Apart from forensic pathology and diagnosis, amplification methods are useful in studying the pathogenesis of disease due to their ability to detect specific DNA sequences that can be correlated with defined pathologic conditions.

From the above discussion, it can be seen that, although many types of nucleic acid hybridization and amplification methods exist, they have several disadvantages.

SUMMARY OF THE INVENTION

The present invention is directed to novel dye-oligonucleotide conjugates and methods of synthesizing them and methods of using them. Methods of using these conjugates or probes involve nucleic acid hybridization methods and nucleic acid amplification methods. The dye portion of the dye-oligonucleotide conjugate is a detectably labeled marker component comprising a fluorophore moiety comprising a luminescent substantially planar molecular structure coupled to two solubilizing polyoxyhydrocarbyl moieties, one located on either side of the planar molecular structure.

Thus, in one aspect, the present invention is directed to a composition comprising an oligonucleotide linked to a detectably labeled marker component which comprises a fluorophore moiety comprising a luminescent substantially planar molecular structure coupled to two solubilizing polyoxyhydrocarbyl moieties, one located on either side of the planar molecular structure.

By "oligonucleotide" is meant a chain of nucleotide residues. Typically, an oligonucleotide useful in the present invention has a length of from 5 to 50 nucleotides. The oligonucleotide probes used in the method of the invention include polynucleotides of DNA, RNA or any other kind of hybridizable to nucleic acid sequences. It will be appreciated that such nucleic acid sequences may include base analogues as well as the naturally occurring bases cytosine, adenine, guanine, thymine and uracil. Such base analogues include hypoxanthine, 2,6-diaminopurine and 8-azaguanine. The probes may be in double stranded or single stranded form but are preferably in single stranded form. They may be prepared by direct synthesis, polymerase mediated extension reactions or by cloning or any other convenient method. By "linked" is meant combined chemically by an intermediate molecule which is connected to both moieties.

In one preferred aspect, the present invention is directed to composition comprising an oligonucleotide linked to a detectably labeled marker component comprising a fluorophore moiety which comprises a substantially planar multidentate macrocyclic ligand coordinated to a central atom capable of coordinating with two axial ligands which are coordinated to the central atom on either side of the macrocyclic ligand.

Marker components used in the immunoassays of the present invention comprise a macrocyclic multidentate ligand having two solubilizing polyoxyhydrocarbyl moieties one located on either side of the plane of the multidentate ligand exhibit no detectable non-specific binding to serum components, and exhibit no detectable solvent sensitivity. These marker components also exhibit enhanced decay times which approach their natural (fluorescent) lifetimes.

Preferred are fluorophores which produce fluorescent light efficiently, i.e., which are characterized by high absorbitivity at the appropriate wavelength and high fluorescence quantum yields. For certain applications, preferred fluorophores have measured fluorescence decay times on the order of at least 2 nanoseconds and exhibit a high degree of fluorescence polarization.

Preferred solubilizing polyoxyhydrocarbyl moieties include water soluble carbohydrates such as glucose, sucrose, maltotriose, and the like; water soluble carbohydrate derivatives such as gluconic acid and mannitol and oligosaccharides; and water soluble polymers such as polyvinylpyrrolidone, poly(vinylalcohol), poly (ethylenimine), polyacrylic acid, polyacrylamide, ethylene oxide copolymers such as Pluronic (a propylene oxide copolymer, available from BASF) and Tetronic (BASF) polyol surfactants; and polyethers, including water soluble polyoxyalkylene polymers, particularly poly(ethylene glycol) ("PEG") and poly(ethylene glycol) derivatives such as poly(ethylene glycol) methyl ether, poly(ethylene glycol) silicon derived ethers and the like.

In one aspect, the present invention is directed to compositions comprising an oligonucleotide linked to a detectably labeled marker component comprising a fluorophore moiety which comprises a substantially planar, multidentate macrocyclic ligand coordinated to a central atom capable of coordinating with two axial ligands and two polyoxyhydrocarbyl moieties which are attached as axial ligands to the central atom. Suitable central atoms are those to which may coordinate two axial ligands and which are not of high enough atomic number to cause extensive fluorescence quenching by transition to the triplet state. Preferred elements for the central atom include silicon, germanium, phosphorus, and tin, especially preferred are silicon and germanium.

Preferably, the detectably labeled marker component has a decay time in the range of from about 1 nanosecond to about 50 nanoseconds, more preferably, the decay time is in the range of from about 5 nanoseconds to about 20 nanoseconds. By "decay time" is meant the time which must elapse in order for the concentration of excited molecules to decrease from its initial concentration to 1/e of that value.

Figure 1:
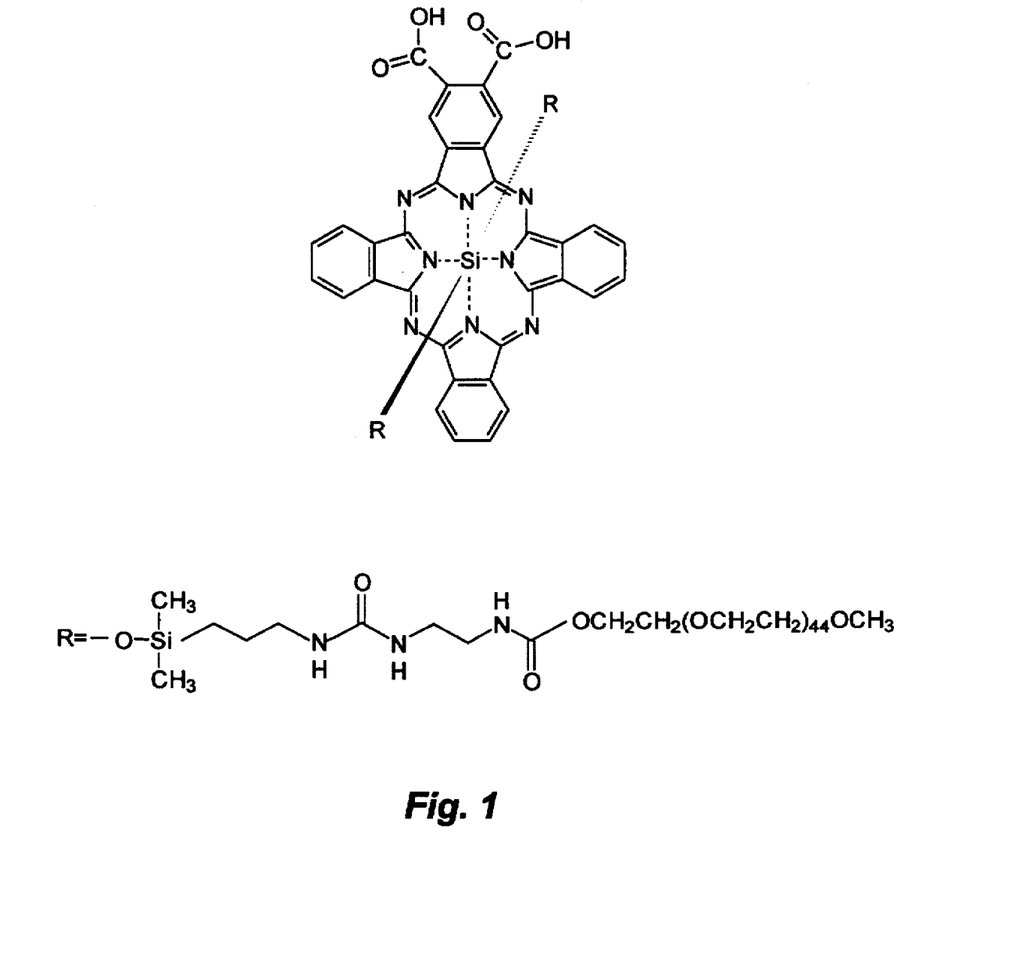
FIG. 1 depicts the structure of the caged dicarboxy silicon phthalocyanine dye.

Particularly preferred is a caged dicarboxy silicon phthalocyanine having the structure depicted in FIG. 1. This dye has an extinction coefficient of $1.7 \times 10^5$ L/mole cm, a quantum yield of 70%, an excitation maximum of 680 nm to 690 nm (depending on the linkage used), and an emission maximum of 705 nm. The caged dicarboxy silicon phthalocyanine dye has the following function group available for coupling: free carboxyl, free primary amino, and N-hydroxysuccinimide (NHS) ester. The dye has a molecular weight of 5,100 g/mole and has a high solubility in aqueous solutions. The dye is also advantageous in that it does not bind significantly to proteins or lipids.

Preferably, the oligonucleotide of the claimed compositions will have a length of about 5 to about 50 bases.

Linkage of the oligonucleotide or polynucleotide to the marker may be accomplished using condensation reactions leading, for example, to the formation of amide, ester, hydrazone, semicarbazone, thiosemicarbazone, urea, and thiourea bonds. For example, a linker may terminate in an amino group, preferably primary. Other linkers may terminate in a carboxyl group.

In another aspect, the present invention provides methods for preparing certain dye-conjugated oligonucleotides. In one embodiment, such a method involves the steps of reacting an oligonucleotide having an attached linker terminating in an amino group with an N-hydroxy succinimide ester or an imidazolide of a detectably labeled marker component which comprises a fluorophore moiety comprising a luminescent substantially planar molecular structure coupled to two solubilizing polyoxyhydrocarbyl moieties, one located on either side of the planar molecular structure, to form a conjugate; and separating the conjugate formed in step (a) from unreacted oligonucleotide or polynucleotide and from unreacted dye. Attachment of a linker to the oligonucleotide can be accomplished by using a diazine or an amino alcohol. Preferably, the detectably labeled marker component comprises the dye shown in FIG. 1, i.e., caged dicarboxy silicon phthalocyanine dye.

Alternatively, preparation of the dye-conjugated oligonucleotides may be accomplished: reacting a detectably labeled marker component which comprises a fluorophore moiety comprising a luminescent substantially planar molecular structure coupled to two solubilizing polyoxyhydrocarbyl moieties, one located on either side of the planar molecular structure, with a carbodiimide in the presence of hydroxybenzotriazole and in the presence of an oligonucleotide or polynucleotide to form a conjugate; and separating the resulting conjugate from other components of the reaction mixture. Preferably, the detectably labeled marker component comprises the dye depicted in FIG. 1, i.e., caged dicarboxy silicon phthalocyanine dye.

In another aspect, the present invention is directed to a method for the detection of a target nucleic acid sequence in a sample comprising the steps of contacting sample nucleic acid with oligonucleotide-labeled marker component, preferably oligonucleotide caged dicarboxy silicon phthalocyanine dye conjugate capable of hybridizing with said target nucleic acid sequence in homogenous solution, and detecting the presence or amount of such hybridization by transient state polarized fluorescence.

In yet another aspect, the present invention is directed to a method for detection of a target nucleic acid sequence in a sample comprising the steps of contacting a sample suspected of containing a target nucleic acid sequence with a complementary oligonucleotide capable of hybridizing with said target sequence; contacting said sample with an oligonucleotide-labeled marker component, preferably oligonucleotide-caged dicarboxy silicon phthalocyanine dye conjugate capable of hybridizing to said complementary oligonucleotide; and detecting the presence or amount of hybridization of said conjugate with said complementary oligonucleotide.

In a further aspect, the present invention is directed to methods for detection or quantification of a target nucleic acid wherein the target nucleic acid is a product of nucleic acid amplification. Nucleic acid amplification methods include polymerase chain reaction (PCR), ligase chain reaction (LCR), self-sustained sequence replication (3SR) and transcript-based amplification system (TAS), which are discussed herein.

In another aspect, the present invention is directed to an improvement in a nucleic acid hybridization method or nucleic acid amplification method comprising employing as a label a fluorescent probe which comprises a detectably labeled marker component which comprises a fluorophore moiety comprising a luminescent substantially planar molecular structure coupled to two solubilizing polyoxyhydrocarbyl moieties, one located on either side of the planar molecular structure. Particularly, preferred is the improvement wherein the detectably labeled marker component is the dye depicted in FIG. 1.

The methods of the present invention are particularly useful when used with a time-correlated transient stage detection system, as described in commonly assigned Studholme, et al., U.S. patent application entitled "Fluorometer Detection System," Ser. No. 07/855,238, filed Mar. 23, 1992. That system features transient detection along with detection of the time-dependent polarization of the sample. The system uses a laser diode which can be modulated at very high frequencies, e.g., 10 MHz rate, and exhibits high output power. Typically the laser "on" time is approximately 2–3 nanoseconds. Photons from the solution are detected using a photomultiplier tube (PMT) operating in a single photon counting mode. The photon event along with the relative time of the photon event as compared with the laser pulse time is determined. By storing the individual photon event times a histogram of frequency of photons as a function of time is generated.

In another aspect, the present invention provides a method for monitoring the kinetics of a nucleic acid amplification process, and/or quantifying nucleic acid in a target sample. For example, during amplification by PCR, a probe consisting of an oligonucleotide which has been both "capped" and labeled with a composition comprising an oligonucleotide or polynucleotide linked to a detectably labeled marker component which comprises a fluorophore moiety comprising a luminescent substantially planar molecular structure coupled to two solubilizing polyoxyhydrocarbyl moieties, one located on either side of the planar molecular structure, may be added directly to the PCR reaction. By "capped" is meant that the 3' end has been reacted dideoxynucleotide.

At each cooling phase, the hybridization with amplified product may be followed kinetically. As the concentration of amplified product increases, the rate of combination of probe with amplified product increases and quantitates the concentration of amplified product. This information together with the number of cycles quantitates the amount of DNA originally in the sample before amplification.

DETAILED DESCRIPTION OF THE INVENTION

The present invention provides nucleic acid probes and methods of making and using the probes. Methods of using the novel nucleic acid probes include various nucleic acid hybridization techniques now known or later developed, and various nucleic acid amplification techniques now known or later developed. The probes (also referred to as conjugates herein) and methods of the present invention allow the achievement of 1 fmole sensitivity in a homogeneous hybridization assay. As demonstrated herein, this sensitivity is comparable to the sensitivity achieved by current heterogeneous hybridization measurement techniques. As noted above, however, current heterogeneous assays have several disadvantages, which result from the many steps involved in the assays, including increased risk of contamination and increased time required to perform the assays. Other advantages of the compositions and methods of the present invention will be apparent to those in the art upon review of the examples provided herein.

I. PREFERRED MARKER COMPONENTS

The following is a brief description of the preferred marker components to be used in the nucleic acid probes and hybridization and amplification methods of the present invention. A more complete discussion is found in commonly assigned U.S. patent applications Ser. Nos. 701,449 and 201,465, which, as noted above, have been incorporated herein by reference.

A. Preferred Fluorophore Moieties

Suitable fluorophore moieties comprise a luminescent substantially planar molecular structure. Preferred are fluorophore moieties in which the luminescent substantially planar molecular structure comprises a substantially planar macrocyclic multidentate ligand which coordinates a central atom which may coordinate with two axial ligands, one on either side of the macrocyclic ligand (i.e. having a trans orientation).

Preferred central atoms are elements which may form octahedral coordination complexes containing two ligands with a trans or axial orientation, on either side and perpendicular to the planar macrocyclic ligand. For use as fluorescent marker components in certain applications the central atom should not have too high atomic number (about 30 or less) so that fluorescence is not diminished through coupling interaction with orbitals of the central atom.

Preferred multidentate ligands include nitrogen-containing macrocycles which have conjugated ring systems with pi-electrons. These macrocycles may be optionally substituted, including substitution on bridging carbons or on nitrogens. Suitable macrocycles include derivatives of porphyrins, azaporphyrins, corrins, sapphyrins and porphycenes and other like macrocycles which contain electrons which are delocalized throughout a system of conjugated electrical orbitals. In view of the fact that they incorporate many of the above-noted characteristics, an especially preferred class of macrocycles comprise porphyrin derivatives, and azzaporphyrin derivatives (porphyrin derivatives wherein at least one of the bridging carbons is replaced by a nitrogen atom). Azaporphyrin derivatives include derivatives of mono-, di- and triazaporphyrin and porphyrazine. These macrocycles may optionally have fused aromatic rings. These azaporphyrin derivatives include phthalocyanine, benzotriazaporphyrin and naphthalocyanine and their derivatives. The preparation and fluorescent qualities of many of these compounds are known and some are available commercially. See U.S. patent application Ser. No. 201,465 and references cited therein, particularly, references 2–5 in that application.

For certain applications, such as fluorescence polarization assays, preferred are azaporphyrin derivatives which exhibit a high degree of polarization, that is, those which emit strongly polarized light. For these applications, preferred are macrocycles having lower degrees of symmetry, preferably having lower symmetry than $D_{4h}$. One preferred group includes macrocycles having at least one fused aromatic ring. Thus, preferred macrocycles include azaporphyrin derivatives having fused aromatic rings at positions which result in decreased symmetry. Preferred classes of azaporphyrin derivatives comprise derivatives of monoazaporphyrin, diazaporphyrin, and triazaporphyrin having lower than $D_{4h}$ symmetry.

B. Preferred Solubilizing Polyoxyhydrocarbyl Moieties

Preferred solubilizing polyoxyhydrocarbyl moieties include water soluble carbohydrates such as glucose, sucrose, maltotriose and the like; water soluble carbohydrate derivatives such as gluconic acid and mannitol, and oligosaccharides; polypeptides such as polysine and naturally occurring proteins; and water soluble polymers such as polyvinylpyrrolidone, poly(vinyl alcohol), poly (ethylenimine), polyacrylic acid, polyacrylamide, ethylene oxide copolymers such as Pluronic™ (a polyether) and Tetronic™ (BASF) polyol surfactants and, in particular, polyethers such as other polyoxyalkylenes including poly (ethylene glycol), or other water soluble mixed oxyalkylene polymers, and the like.

A particularly preferred class of solubilizing polyoxyhydrocarbyl moieties comprises poly(ethylene glycol) (PEG) and poly(ethylene glycol) derivatives, such as poly(ethylene glycol) monomethyl ether. Other suitable PEG derivatives include PEG-silicon derived ethers. Many of these polymers are commercially available in a variety of molecular weights. Others may be conveniently prepared from commercially available materials, such as by coupling of an amino-PEG to a haloalkyl silyl or silane moiety. When linked to a fluorophore moiety, these polyoxyhydrocarbyl moieties impart particularly advantageous qualities of solubility in aqueous solution with improved measured fluorescence decay time, and improved fluorescence intensity. Moreover, the resulting marker components are water soluble and show decreased non-specific binding, especially decreased binding to serum albumin which has heretofore been a problem with certain fluorophores, particularly porphyrin or phthalocyanine dyes which have been functionalized with groups such as sulfonate to impart increased water solubility to the molecule. Non-specific binding of fluorophore or marker component impairs the accuracy of the resulting immunoassay. These marker components which comprise fluorophore linked to PEG may also exhibit improved fluorescence intensity in aqueous solution with decreased quenching.

Suitable PEGs may vary in molecular weight from about 200 to about 20,000 or more. Choice of a particular molecular weight may depend on the particular fluorophore chosen and its molecular weight and degree of hydrophobicity, as well as the particular application for which the fluorophore-PEG complex is to be used.

The dye structure depicted in FIG. 1 consists of a dicarboxy phthalocyanine with a central silicon atom having two axial ligands each consisting of one polyethylene chain bonded to the central atom by siloxane bonds. The polyethylene chains serve to "cage" the phthalocyanine moiety.

C. Absorbance and Polarization Behavior of Preferred Marker Components

These marker components which comprise a central atom (for example, silicon) coupled to two PEG moieties may be characterized by measurements of transient state fluorescence. In such measurements the intensity of the two components polarized either parallel or perpendicular to the direction of polarization of the exciting pulse is monitored over a time period equal to about 3 times the decay time of the marker component. Such curves reflect extinction coefficient, quantum yield, decay time and state of polarization and supply sensitive indications on the chemical and physical condition of the marker component.

For example, if the excited state is being deactivated or converted to the triplet state the overall intensities are lowered and the decay times shortened. If the rotary brownian motion of the molecule is being altered by an increase in viscosity or by being bound to a large molecule, the ratio of the intensity of the parallel to the perpendicular component is increased.

Some marker components according to the present invention show, within experimental error of about 5%, the same intensities, decay time and polarization in DMF (an organic solvent) as in SAP (saline azide phosphate, an aqueous neutral buffer). To some extent these properties are shared by other marker component preparations. A distinctive and important property of the marker components of the present invention is a insensitivity to (and lack of binding to) the components in serum which is evidenced by a lack of any measured effect of serum on the intensities, decay time or relative magnitudes of the polarized components of the fluorescence. This property is crucial for the marker components to be useful for applications such as assays using biological materials.

D. Preparation of Preferred Marker Components

According to one method of preparing the preferred marker components of the present invention, the appropriate fluorophore moiety having hydroxy or halide groups as axial ligands is reacted with a reactive form of the solubilizing polyoxyhydrocarbyl moiety in a ligand exchange reaction according to the general reaction scheme:

Mcl-CA-(X)$_2$+2(SM)→Mcl-CA-(SM)$_2$+2X wherein Mcl denotes the macrocyclic ligand, CA the central atom, X the displaced ligand and SM the solubilizing moiety. This reaction may be carried out neat or, if desired, in solvent. Suitable solvents include quinoline, THF, DMF, imidazole and the like. Suitable reaction temperatures may vary, depending on the nature of the macrocyclic starting material and the solubilizing group. The reaction is generally complete in about 2 minutes to about 24 hours. The reaction mixture can be conveniently heated under reflux or by means such as a sand bath. For convenience, the reaction may be carried out at ambient pressure.

It is believed that this reaction takes place in two steps, with one polyoxyhydrocarbyl group coordinating as an axial ligand at a time.

EXAMPLE 1

Preparation of a Caged Dicarboxy Silicon Phthalocyanine Dye

Unless otherwise stated, all chemicals used in the this Example 1 were purchased from Aldrich Chemical Co., Milwaukee, Wis. Amino-terminated polyethylene glycol and phthalocyanine derivatives were synthesized according to published procedures. See, e.g., Reference 18 of U.S. patent application Ser. No. 701,449.

A. Preparation of Diiminoisoindoline

In a three-neck, 100 ml round-bottom flask fitted with a reflux condenser and a gas inlet tube was placed phthalonitrile (12.8 g), and methanol (50 ml), and the mixture was stirred while ammonia gas was slowly introduced. In order to prevent the possible flow of the reaction mixture into the ammonia source, and in-line trap was employed. After the reaction mixture appeared to be saturated with ammonia, 0.33 g of dry potassium tert-butoxide was added with stirring.

Stirring was continued and the reaction mixture was heated to reflux for three hours with continued introduction of ammonia. Care was taken to avoid fouling of the gas inlet with the crystalline product. At the end of the reflux period a pale green solid had formed. The solid was collected by filtration and washed with a small volume of cold (4° C.) methanol. (This compound is appreciably soluble in methanol.) This material was dried and used for the next step without further purification. Yield was 7 g (about 50%).

B. Preparation of Dicyanodiiminisoindoline 1,2,4,5-Tetracyanobenzene (Pfaltz & Bauer, 0.5 g, 2.8 mMol) was suspended in methanol (10 ml) in a three-neck round-bottom flask fitted with a reflux condenser and a gas inlet tube. The mixture was stirred at 25° C. without external cooling while ammonia gas was rapidly introduced. During the first two minutes of ammonia introduction the temperature of the reaction mixture rose to greater than 50° C. and the suspended solid dissolved completely. Within 5 minutes a precipitate began to form. Stirring at 40°–50° C. with slow introduction of ammonia was continued for 1 hour. The precipitated solid was collected by filtration, washed with methanol, and dried. This product exhibited a very low solubility in methanol.

C. Preparation of Dicyanosiliconphthalocyanine Dichloride (Compound I)

In a dry 50 ml round-bottom flask was placed dicyanodiiminoisoindoline (350 mg, 1.8 mMol) along with diiminoisoindoline (1.0 g, 6.9 mMol) and quinoline (Fluka, 20 ml). The mixture was stirred at 25° C. while silicon tetrachloride (Aldrich, 2.0 ml, 18 mMol) was added dropwise over a period of 1 minute. The flask was then fitted with a reflux condenser (using teflon tape) and a calcium chloride drying tube and stirred for one minute at 25° C.

At this time the reaction flask was lowered into a large oil bath maintained at 180°–185° C. and efficient magnetic stirring was continued for 30 minutes. The oil bath was then removed and the contents of the flask were allowed to cool to room temperature.

The dark reaction mixture was carefully treated with water (5 ml) and then diluted with 45 ml of a 30% HCl solution. The resulting dark precipitate was collected by filtration on a 10 cm Buchner funnel. Washing with water and then acetone left a blue solid (1 gram) which was air dried and used without further purification for the next reaction step.

D. Hydrolysis of Dicyanosiliconphthalocyanine Dichloride (Compound II)

The crude dicyanophthalocyanine from step (C) (1 gram) was placed in a flask with a stir bar and 6 ml of concentrated sulfuric acid and stirred at 50° C. overnight. The mixture was then carefully diluted with 4 ml water and heated to 100° C. for an additional 20 hours. Cooling and dilution with water (20 ml) gave a blue precipitate which was collected by filtration and washed with water. The solid was then transferred to a flask along with a stir bar and 20 ml of a 1.0M potassium carbonate solution and stirred and heated at reflux for one hour. The suspension was then slowly and carefully acidified with concentrated HCl and then filtered and the resulting solid was washed with water and acetone and dried in a desiccator. This material (0.7 g) was used without further purification in the next step.

E. Preparation of 2,3-Dicarboxyphthalocyaninato-bis-[3-(1H-imidazol-1-ylcarbonyl)aminopropyl-dimethylsilanolato] silicon (Compound III)

The crude dicarboxy silicon phthalocyanine dihydroxide from step (D) (85 mg) was placed in a vial along with a stir bar and imidazole (160 mg, 2.3 mMol) and 1 ml of dry DMF. The mixture was stirred for 5 minutes at 25° C. and then 3-isocyanatopropyldimethylchlorosilane (Petrarch, 110 µl, 0.68 mMol) was added to the stirred mixture over a period of 0.5 minutes. The vial was capped in order to exclude moisture and stirring at 25° C. was continued for 20–40 hours. (A 40 hour reaction time appeared to result in an improved yield.) The vial was then opened and the dark blue mixture was diluted with methanol (4 ml) and filtered through #545 celite to remove solids. The filtrate was concentrated on a rotovap using high vacuum and a water bath maintained at 40° C. The dark residue was then slurried with silica gel (1–3 g) and methanol (5 ml) and the methanol was removed on a rotovap under aspirator pressure. The blue residue was then suspended in toluene and transferred to a silica gel column prepared from 15 ml 23–400 mesh silica gel (EM Science) and toluene. This column had been washed with 50% methanol in toluene.

Increasing the solvent polarity by increasing the methanol content of the solvent to 16% brought about the migration of a distinct band which was collected. This material was saved but not used for further transformations.

Increasing the solvent polarity by slowly increasing the methanol content of the eluant to 30% brought about the migration of a second blue band which was collected within a 20 ml volume of 30% methanol. This material was transferred to a round bottom flask. Removal of solvent on a rotovap under high vacuum at 25° C. left a residue which appeared to include an appreciable quantity of imidazole along with the blue dye. This material was used without further purification for the next step. The yield of compound III was approximately 3 mg.

F. Preparation of Amine-Terminated Polyethylene Glycol

Poly(ethylene glycol) monomethyl ether (Aldrich, average M.W. 2000, 10 g, 5 mMol) was placed in a 100 ml round-bottom flask along with a stir bar and 55 ml toluene. The flask was fitted with a short-path distillation apparatus and immersed in a heating bath. Toluene was slowly distilled at 760 mm Hg until the distillate was no longer cloudy. This required the removal of about 15 ml of toluene.

The relatively water-free PEG solution was allowed to cool to 40° C. When this temperature had been attained, carbonyldiimidazole (Aldrich, 1.2 g, 7.5 mMol) was added to the stirred solution in one portion. Stirring at 30°–40° C. was continued overnight with protection from atmospheric moisture.

Water (100 µl, 3.75 mMol) was then added to the reaction mixture and efficient magnetic stirring was continued until the evolution of $CO_2$ gas could no longer be observed (about 15 minutes).

Most of the toluene was removed on the rotovap at 30° C. under high vacuum leaving a viscous, colorless oil. This material was diluted with isopropanol (20 ml) and added to a stirred solution of 1,2 ethylenediamine (Fluka, 6.7 ml, 100 mMol) in isopropanol (15 ml) over a period of five minutes. After completion of the addition the clear solution was maintained at 40° C. for four hours.

At this time isopropanol (150 ml) was added to the reaction mixture. The diluted solution was allowed to stand at 4° C. overnight, resulting in the formation of a voluminous mass of white crystals. This solid was collected on a 10 cm Buchner funnel, and subsequently recrystallized from isopropanol.

Drying under high vacuum over sulfuric acid afforded 7 grams of the crude amine, suitable for use as a reagent. Structure of the product was confirmed by IR.

The amine content of polyethyleneglycol amine, prepared as outlined above, was determined to be >70 mole % by the following method:

25 ml of 10% solution of the amine in methanol was allowed to react with an equal volume of a 6% solution of maleic anhydride in THF. The reaction mixture was allowed to stand for 0.5 hours at 25° C. and was then diluted to 1.0 ml with methanol. A 5 µl aliquot of this final solution was injected on to an analytical RP18 reverse phase HPLC column using 30% methanol in water as the initial mobile phase. Using n-propylamine as an internal standard allowed for accurate-quantification of the UV-absorbing acyl-PEG derivative, which was eluted in 80% methanol and was detected at 254 nm.

Analysis of the infrared spectrum of amine-terminated PEG can also provide a convenient means of estimating the product yield.

G. Reaction of Compound III with Amine-Terminated Polyethylene Glycol (Compound IV)

The product of step (E) (Compound III) (3 mg, $5\times10^{-3}$ mMol), which had been obtained in partially purified form by chromatography on silica gel, was dissolved in methanol (1 ml). The mixture was stirred while amine-terminated PEG (product of step (F), 100 mg, $5\times10^{-2}$ mMol) was added. The resulting deep blue solution was heated to reflux for one hour.

Removal of methanol under aspirator pressure at 25° C. left a viscous blue oil which was taken up in water (0.5 ml) and applied to a small (10 ml wet volume) DEAE Sephadex anion ion exchange column (Pharmacia, 3.5 meq/g, 40–120 micron, basic form <1M $K_2CO_3$). The water-soluble blue dye was retained quantitatively by the column. The column was washed with water (15 ml) and the blue dye was then eluted in greater than 70% yield with 10–20 ml of a 15% aqueous acetic acid solution.

Water and acetic acid were removed under high vacuum and the blue residue was taken up in a small volume of methanol and applied to a C18 reverse phase semi-preparative HPLC column. The major product, detected at 675 nm as a single peak, eluted with 80% aqueous methanol (containing 0.6% acetic acid) and comprised about 50% of the sum of the material which was recovered from the column. Fractions containing the major product were combined and solvent was removed under high vacuum leaving a blue residue (approx. 0.5 mg, $10^{-7}$ mMol).

NMR (DCCl$_3$: δ–2.85 (5, 12H), δ–2.29 (m, 4H), δ–1.30 (m, 4H), δ 1.80 (m, 4H), δ 3.6 (br.s, 300–400H), δ 8.39 (m, 6H), δ 9.68 (m, 6H), δ 10.56 (S, 2H). Note: Because the sample had been previously dissolved in D$_2$O, the acidic protons, RCOOH, were not observed.

II. NUCLEIC ACID PROBES AND METHODS

Reagents and Instrumentation.

Unless otherwise stated, reagents and instrumentation used in the following Examples 2–13 are as follows:

Phosphoramidites and Aminolink-2 reagent used in DNA synthesis were purchased from Applied Biosystems (Foster City, Calif.). The 20×SSP buffer contained 3.6M NaCl, 200 mM Na$_2$PO$_4$, pH 7.4. T4 Kinase (EC 2.7.1.78) was obtained from New England Biolabs Inc., MA. DMSO and sorbitol (molecular biology grade) were obtained from Sigma Chemical Co., St. Louis, Mo., and dextran sulfate (sodium salt) was purchased from Pharmacia, Uppsala, Sweden. N-Methyl-2-pyrrolidone was obtained from Fluka and stored over 4A and 5A sieves. All solutions used in handling RNA were treated with 0.1% (v/v) of dimethyl pyrocarbonate (DEPC) and autoclaved to inactivate RNases. Derivatization of oligonucleotides and hybridization reactions were performed in presiliconized microcentrifuge tubes which were obtained from Denville, (Denville Scientific, Denville, N.J., Cat# C19033). Radioactivity was measured by Cerenkov counting using a Beckman LS 7800 liquid scintillation counter. Oligonucleotides and the caged dicarboxy silicon phthalocyanine-conjugated derivatives were quantitated on the basis of their absorbances at 260 and 680 nm with a Beckman DU-7400 or Perkin Elmer Lamda 4C UV-visible Spectrophotometer. Caged dicarboxy silicon phthalocyanine dye was synthesized by Diatron Corporation. All other reagents were obtained from Aldrich Chemical Corp. (Milwaukee, Wis.).

Fluorescence polarization measurements were performed on Diatron Corporation's Transient State Fluorometer which uses a 685 nm laser diode (Toshiba Model TOLD9140) to excite the sample. The laser diode was pulsed on for 2 ns at a 10 MHz repetition rate and a thermal controller was used to maintain the diode temperature at 40° C., +/−0.1° C. The output optics consisted of an optical filter centered at 705 nm, a liquid crystal polarizer and a photomultiplier tube (Hamamatsu Model R2949). Emission from the sample was detected using time-correlated single photon counting (10) with a resolution of 75 ps. Each sample was viewed for 10 s with the output polarizer oriented parallel, then perpendicular to the excitation polarization. In this way two histograms representing the parallel and perpendicular fluorescence decay profiles were obtained. The two fluorescence components S(parallel) and S(perpendicular) were calculated from the time histogram data by summing the total counts over a portion of the data where the transient state fluorescence signal has the highest signal-to-background ratio. The transient state (TS) polarization is expressed in millipolarization units (mP) as:

$$TS\ Polarization(mP) = 1000 * \frac{(S(\text{parallel}) - S(\text{perpendicular}))}{(S(\text{parallel}) + S(\text{perpendicular}))}$$

The transient state instrumentation was configured to automatically read up to 12 reaction tubes with a volume of 1 mL or 100 μL. The optical system was thermally controlled at 35° C., +/−0.1° C. Dedicated microprocessors were used to control mechanism movements, temperature and transient state data acquisition.

EXAMPLE 2

Oligonucleotide Synthesis and Linker Attachment

Oligonucleotides were synthesized on an Applied Biosystems 394 DNA/RNA synthesizer using standard phosphoramidite chemistry. The hexylamine-linked oligonucleotides were synthesized by using the AminoLink2 reagent in the last step of the automated synthesis. The ethylamine-linked oligonucleotide derivative was prepared by a two-step procedure from 5' hydroxyl oligonucleotides. The tritylated and 5'-aminohexyl oligonucleotides were purified by reverse-phase HPLC according to Ishii and Ghosh, *Bioconjugate Chem.* 4(1):34–41 (1993). The purified oligonncleotides migrated as single bands on a 15% denaturing polyacrylamide gel. The sequences of the oligonucleotides are as follows:

| | |
|---|---|
| 90-422: | 5'-AATTAGGCCAGTAGTATCAACTCAACTGCT-3' |
| 86-272: | 5'-TCTAATTACTACCTCTTCTTCTGCTAGACT-3' |
| 92-157: | 5'-AGCAGTTGAGTTGATACTACTGGCCTAATT-3' |
| 86-273: | 5'-AGTCTAGCAGAAGAAGAGGTAGTAATTAGA-3' |
| 89-255: | 5'-TTATTGTGCCCCGGCTGGTTTTGCGATTCTA-3' |
| 89-263: | 5'-<u>AATTTAATACGACTCACTATAGGG</u>ATTTTAA-AGTGTTATTCCATTTTGCTCTACT-3' |
| 88-336: | 5'-TTCACCTTGCCCCACAGGGCAGTAACGGCA-3' |

Underlined bases in oligonucleotide 89-263 denote the presence of a T7 promoter sequence. The transcription initiation sequence is in boldface.

EXAMPLE 3

Oligonucleotide-Dye Conjugate Synthesis and Purification

Oligonucleotide 90-422 (~500 nmol) was dissolved in 250 μL of 0.2M collidine, buffer pH 7.7 in a 1.5 mL Denville centrifuge tube. After addition of 25 μL of 8M lithium chloride (LiCl) and 825 μL of absolute ethanol, the mixture was cooled in dry ice and centrifuged at 14,000 rpm in a centrifuge at 0° C. After removal of the supernatant, the pellet was redissolved in 1.3 mL of collidine buffer. A 100-μL aliquot (40 nmol) of the oligonucleotide solution was added to a dried sample (400 nmol) of the bis-N-hydroxysuccinimide ester of caged dicarboxy silicon phthalocyanine dye in a centrifuge tube. Following addition of 25 μL of 8M LiCl and 50 μL of collidine buffer, the mixture was cooled to 0° C. 75 μL of N-methylpyrrolidone were then added, and the reaction mixture was incubated at room temperature for 1 hour and then maintained at 4° C. for a further 18 hours. Absolute ethanol (750 μL) was added and the reaction products were precipitated. The pellet containing the conjugate and unreacted oligonucleotide was redissolved in 100 μL of collidine buffer. HPLC purification was performed on a C8 reversed phase analytical column, 4.6× 250 mm, using a gradient of acetonitrile in 0.1M triethylammonium acetate, pH 6.8. Effluent was monitored at 675 nm. Comparison of the absorbances at 260 and 680 nm of the purified dye-oligonucleotide conjugates indicated an equimolar oligonucleotide-to-dye ratio (data not shown).

Figure 2:
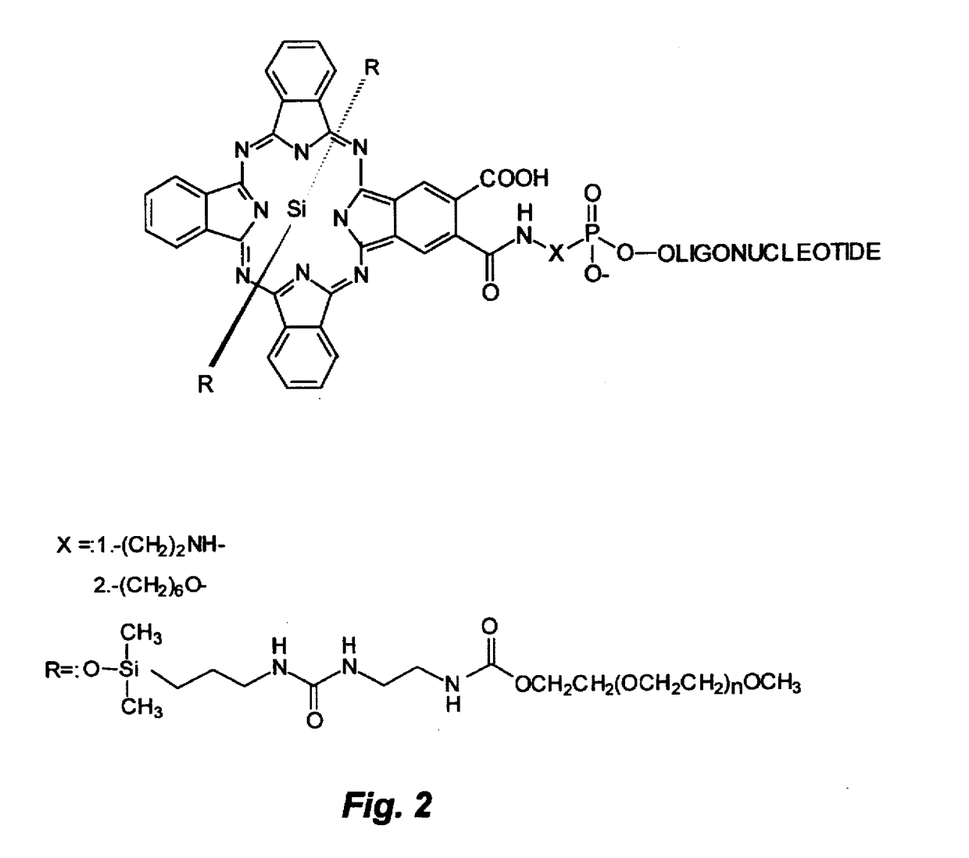
FIG. 2 depicts oligonucleotide linked to caged dicarboxy silicon phthalocyanine dye.
Figure 3:
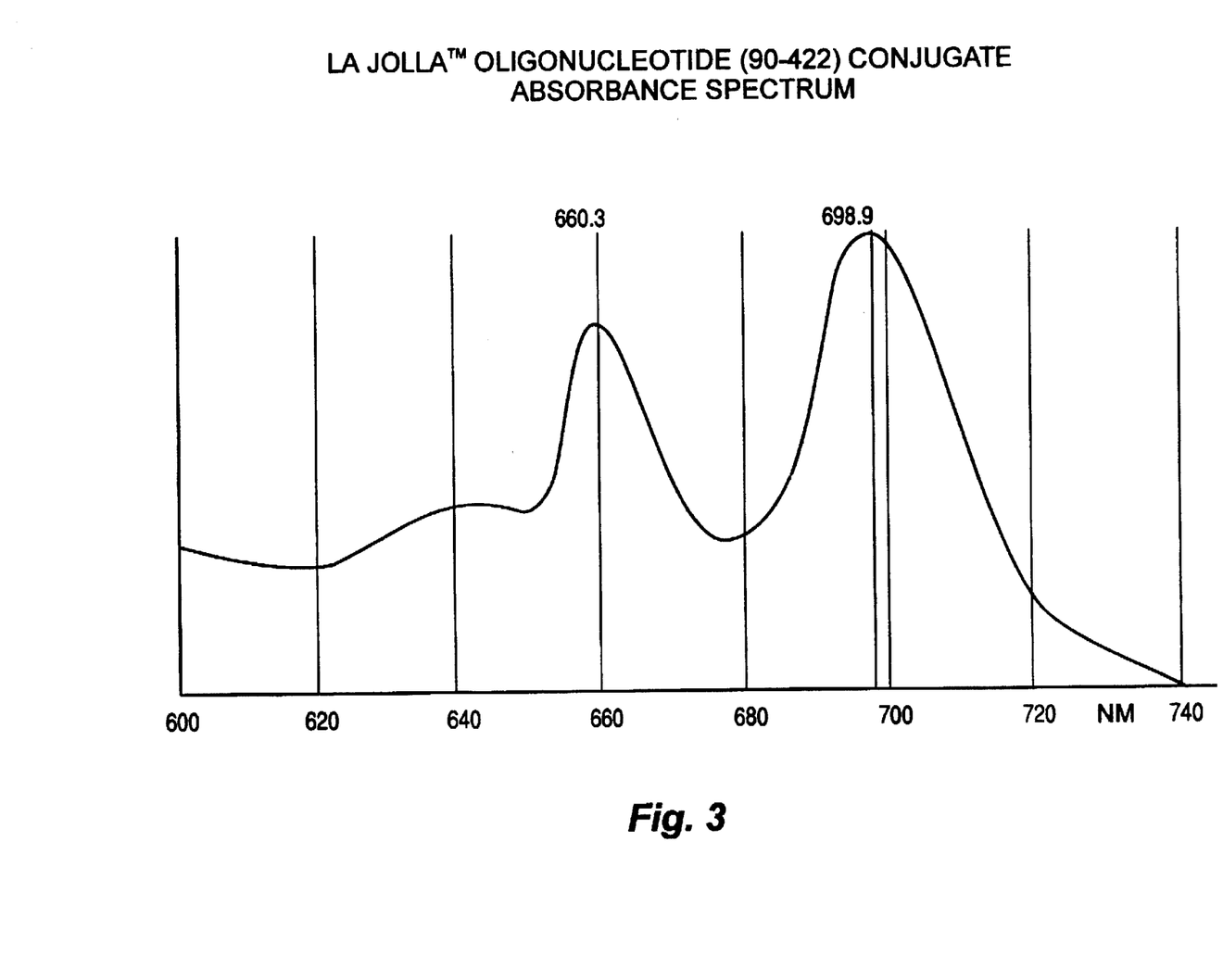
FIG. 3. depicts an absorption spectrum for caged dicarboxy silicon phthalocyanine dye-oligonucleotide 90-422 conjugate.

Resulting oligonucleotide-dye conjugates have the general structure shown in FIG. 2. When a hexylamine-linked oligonucleotide is used, the X group in the resulting linker is $(CH_2)_6O$. When an ethylamine-linked oligonucleotide is used, the X group in the resulting linker is $(CH_2)_2NH$. A typical absorbance spectrum of a caged dicarboxy silicon phthalocyanine-oligonucleotide conjugate is shown in FIG. 3. Of course, those in the art will realize that other types of linked oligonucleotides may be used in place of the hexylamine-linked or ethylamine linked oligonucleotides. For example, the length of the hydrocarbon chain may be modified, and other reactions may be suitable, for example, the terminating group may be chosen to form ester, amide, hydrazone, semicarbazone, thiosemicarbazone, urea or thio-urea.

EXAMPLE 4

3SR Amplification of HIV-1 RNA

The oligonucleotide primers 89-255 and 89-263 were used to amplify a 382-base length region of the env gene of HIV-1 RNA, as described by Fahy et al., *PCR Methods and Applications* 1:25–33 (1991). Briefly, the 3SR reaction consists of continuous cycles of reverse transcription and RNA transcription designed to replicate a nucleic acid using a double-stranded cDNA intermediate. Oligonucleotides A and B primer DNA synthesis producing a double-stranded cDNA containing a functional T7 promoter. Complete cDNA synthesis is dependent upon digestion of RNA in the intermediate RNA-DNA hybrid by RNase H. Transcription-competent cDNAs are used to produce multiple (50–1000) copies of antisense RNA transcript of the original target. These antisense transcripts are immediately converted to T7 promoter-containing double-stranded cDNA copies and used again as transcription templates. This process continues in a self-sustained cyclic fashion under isothermal conditions (42° C.) until components in the reaction become limiting or inactivated (enzymes). The target used was 0.1 amol of HIV-1 RNA extracted from infected CEM cells (Kwoh et al., *Proc. Natl. Acad. Sci. USA* 86:1173–1177 (1989)). The amplification reactions contained 10% (v/v) DMSO and 15% (wt/v) sorbitol and were carried out in a volume of 50 μL for 1 hour.

EXAMPLE 5

Synthesis of Aminoethyl Oligonucleotide Derivative

Oligonucleotide 90-422 (10 nmol) was phosphorylated with T4 kinase and gamma-$^{32}$P-ATP using standard procedures, as described, for example, in Maniatis et al., *Molecular Cloning: A Laboratory Manual*, Cold Spring Harbor, N.Y., 1982. The phosphorylated oligonucleotide derivative was dissolved in 200 μL of a solution containing 0.1M 1-methyl imidazole, 0.1M 1-ethyl-3-(3-dimethylaminopropyl)carbodiimide. HCl and 0.25M ethylenediamine, pH 6.0. After 16 hours at room temperature the reaction mixture was precipitated twice with LiCl/ethanol and redissolved in 10 mM Tris HCl, 1 mM EDTA, pH 7.4.

EXAMPLE 6

Detection of 3SR RNA Product By Sandwich Hybridization

Oligonucleotide 86-273 was attached to Trisacryl GF-2000 support as described by Davis et al., *J. Infect. Dis.* 162:13–20 (1990). Serial dilutions of the 3SR RNA product were assayed by bead-based sandwich hybridization (Fahy et al., *PCR Methods and Applications* 1:25–33 (1990) with Trisacryl derivatized with oligonucleotide 86-273, and $^{32}$P-labeled oligonucleotide 90-422 (100 fmol) was used as the detection probe. In this study, the transient state fluorescence method was compared to a Bead Based Sandwich Hybridization system (BBSH). Briefly, a Trisacryl resin-bound 30-mer oligonucleotide, complementary to the 3SR generated RNA, was used as the capture sequence and $^{32}$P labeled 90-422 oligonucleotide, which is complementary to another region of the 3SR RNA product, was used as the detection probe. The Trisacryl-oligonucleotide beads and the detection oligonucleotide were used in a hybridization reaction with the 3SR RNA target at 42-C for 60–90 minutes. Excess probe was washed away and the radioactivity associated with the solid support was used to estimate the amount of hybridized target.

EXAMPLE 7

Fluorescence Polarization Assays

The desired amount of conjugate was dissolved in 5 μL of probe buffer [100 mM $Na_2HPO_4$, pH 7.5, 175 mM NaCl, 0.05% (w/v) Tween 20, 0.1% (w/v) PEG 2000], and mixed with 10 μL of the DNA or RNA analyte in DEPC-treated $H_2O$ and 15 μL of hybridization buffer [10×SSP, 20% (w/v) dextran sulfate]. Hybridizations were performed under the various conditions described in the results section. After a brief centrifugation of the samples to remove condensation, 70 μL (or 1 mL where noted) of read buffer (100 mM $Na_2HPO_4$, 150 mM NaCl, pH 7.5) was added, the solutions were transferred to glass cuvettes and the transient-state fluorescence polarization values were measured. Measurements were made in a transient-state fluorometer using a pulsed 685 nm laser diode to excite the sample. The laser diode was pulsed on for 2 ns at a 10 MHz repetition rate. A thermal controller was used to hold the diode temperature to 40° C.+/−0.1° C.

The output optics consisted of an optical filter centered at 707 nm, a liquid crystal polarizer and a photomultiplier tube. Emission from the sample was detected using time correlated single photon counting with a resolution of 75 ps. Each sample was viewed for 10 seconds with the output polarizer oriented parallel, then perpendicular to the excitation polarization. In this way two histograms representing the parallel and perpendicular fluorescence decay profiles were obtained.

These histograms were analyzed to obtain S (parallel) and S (perpendicular) light components by summing the total counts over a portion of the data where the transient-state fluorescent signal has the highest signal-to-background ratio.

After a preset period of time a histogram of counts as a function of bin number was obtained. Steady-state fluorescence information was obtained during the time of the laser pulse, with the transient-state information coming after the laser pulse has been turned off.

Data obtained in this manner can be analyzed as described in Dandliker et al., U.S. Pat. No. 4,877,965, entitled "Fluorometer" or as described by Studholme, et al., U.S. patent application entitled, "Fluorometer Detection System," Ser. No. 07/855,238, filed Mar. 23, 1992.

EXAMPLE 8

Kinetic Reactions

Figure 4:
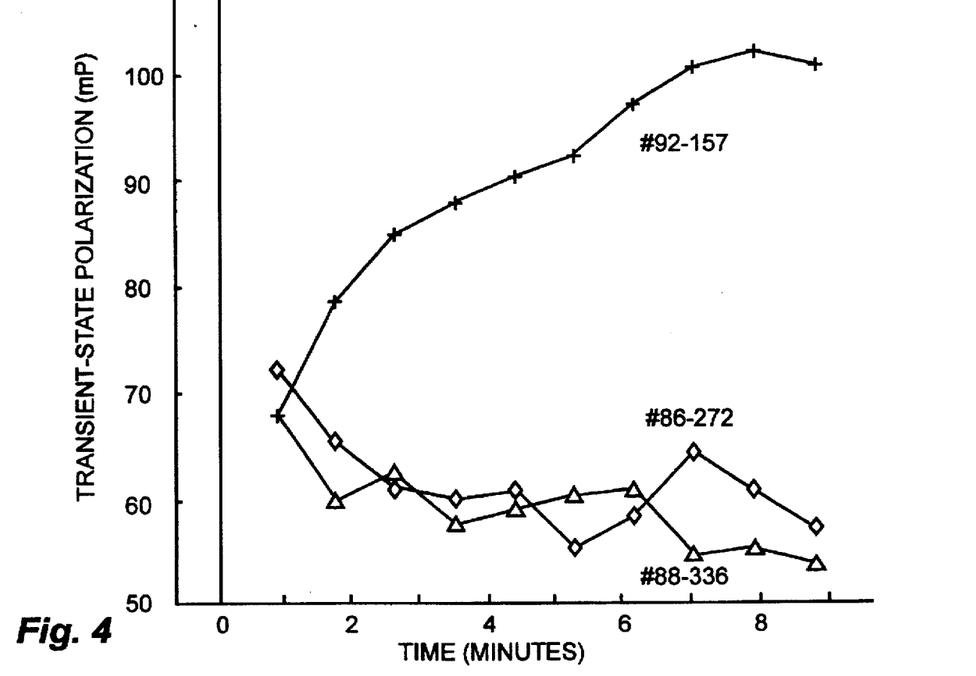
FIG. 4 depicts hybridization as a function of time for complementary and noncomplementary oligonucleotides. Oligonucleotide 92-157 is complementary to the dye conjugated (labeled) oligonucleotide 90-422 and, thus, the transient state polarization increases with time as the two oligonucleotides hybridize. Oligonucleotides 88-336 and 86-272 are noncomplementary.

The time-course of the hybridization reactions of the conjugate containing the 30-base hexylamine-derivatized oligonucleotide 90-422 (350 fmol) with a 25-fold molar excess of complementary and non-complementary 30-base oligonucleotides was studied by acquiring transient state polarization measurements at 49-second intervals. As shown in FIG. 4, when the oligonucleotide 92-157 is used as the complementary target, the fluorescence polarization values increase with time and reach a maximum after 8 minutes. In contrast, the fluorescence polarization values obtained for the reactions with non-complementary oligonucleotides show no time-dependent increase from their initial values, at time zero. These experiments demonstrate that hybridization reaction kinetics can be measured in real time and with high sensitivity.

EXAMPLE 9

Oligonucleotide Titration Study

Figure 5:
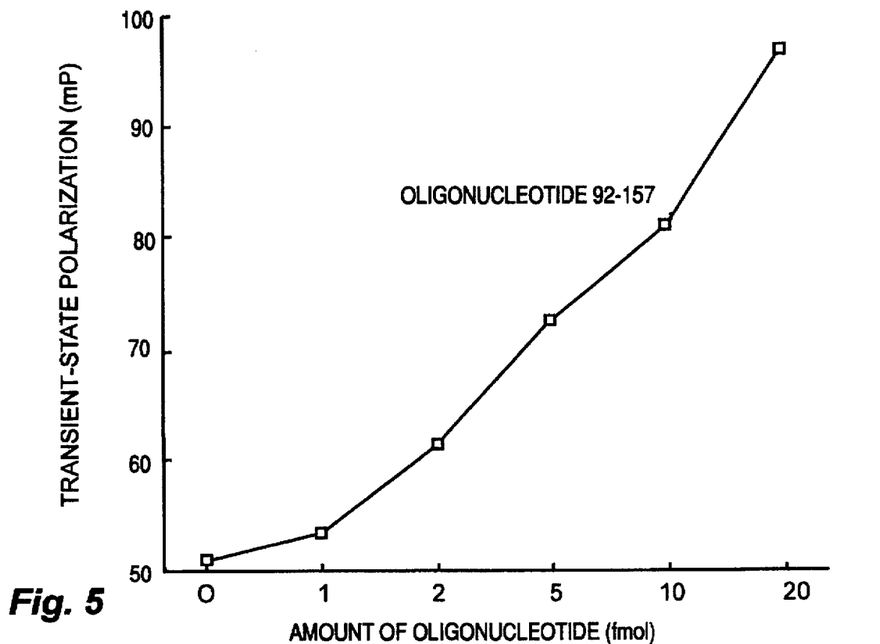
FIG. 5 depicts hybridization of complementary oligonucleotide 92-157 titrated from 20 fmol to 1 fmol. For example, 5 fmol of probe (labeled oligonucleotide 90-422) was incubated for 45 minutes at 42° C. with varying levels of the complementary oligonucleotide 92-157. 100 µL of read buffer was added prior to reading.

FIG. 5 depicts the results of a representative titration experiment in which a 45-minute hybridization of 5 fmol of probe with increasing amounts of complementary oligonucleotide was monitored by fluorescence polarization. The level of sensitivity achieved in this experiment was approximately 1 fmol. No improvement in the sensitivity of the assay was observed when an ethylamine group was substituted for the hexylamine group in the conjugate (data not shown).

EXAMPLE 10

Detection of Complementary RNA: Transient State Titration Curve

Figure 6:
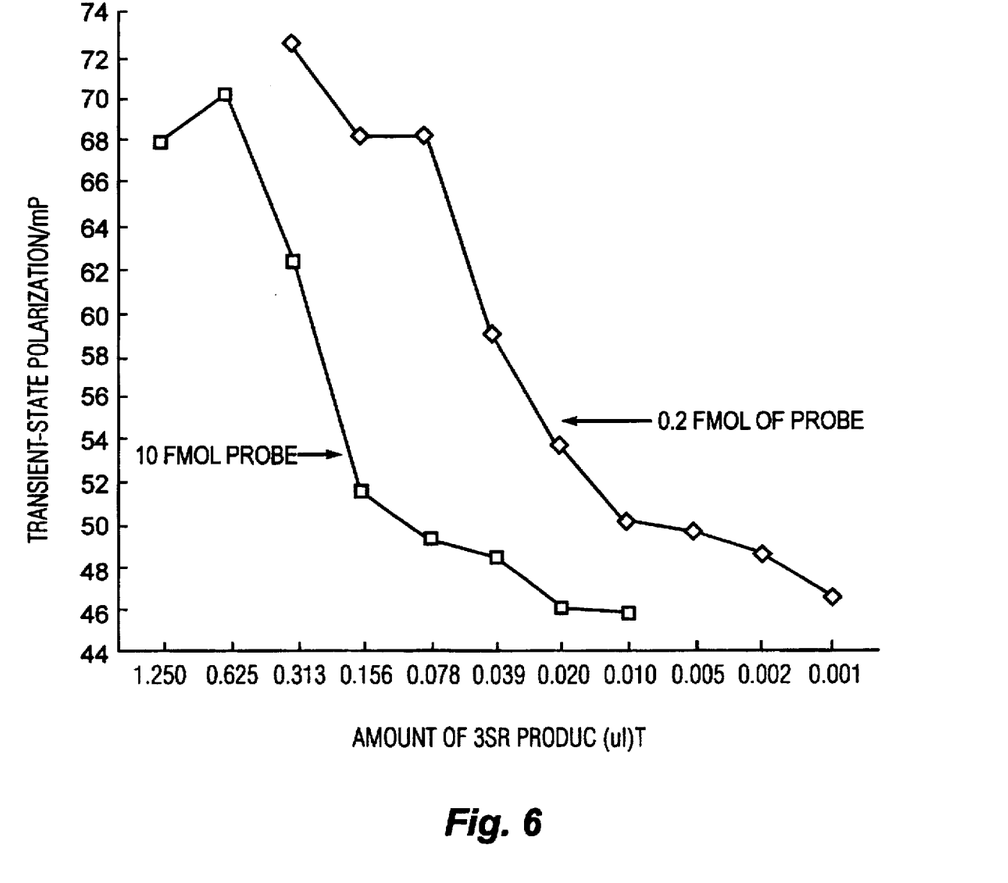
FIG. 6 depicts the sensitivity for detection of 3SR RNA product with probe (labeled oligonucleotide 90-422) levels of 10 fmol and 0.2 fmol. The reaction mixtures were incubated at 60° C. for one hour. Sensitivity was shown to be 16 fmol and 2 fmol, respectively. The amount of 3SR RNA product in the stock solution was 1000 fmol/µL. 10 µL of diluted stock was reacted with 15 µL of buffer and 5 µL of probe for a total volume of 30 µL in the reactions. Readings were performed after dilution of the final reaction to 100 µL.

An antisense 382-base length RNA transcript of the env gene of HIV-1 was generated by 3SR amplification and was detected with the complementary caged dicarboxy silicon phthalocyanine dye-oligonucleotide 90-422 conjugate. The rate of hybridization was observed to be slower with this more complex target (data not shown), and hence, assays were typically conducted for 1 hour at 60° C. The dynamic range and the limit of sensitivity of transient state polarization fluorescence (TSPF) method was determined by incubating aliquots of the target RNA solution (1000 fmol/μL) with two different amounts (10 and 0.2 fmol) of conjugate probe. The results shown in FIG. 6 indicate that, although the limit of sensitivity with 10 fmol of conjugate probe was approximately 16 fmoles (0.016 μL) of the target RNA, as little as 2 fmol (0.002 μL) of the same RNA solution could be detected with 0.2 fmol of conjugate-probe. At this lower probe concentration, the high intensity of the fluorescence signal (>100,000 photon counts/20 s) ensured highly reliable counting statistics.

The observed sensitivity of transient state fluorescence is comparable to that of bead-based heterogeneous methodology, to time-resolved fluorescence utilizing lanthanade based chelates, and to bead-based alkaline phosphatase linked chemiluminescence assays. However, in contrast to heterogeneous methods which can use only 20% of the 3SR reaction, use of caged dicarboxy silicon phthalocyanine dye and transient state fluorescence can utilize the entire amount of 3SR amplified reaction product, resulting in an additional approximately 5-fold increase in sensitivity.

EXAMPLE 11

Detection of Complementary RNA By Sandwich Hybridization

Figure 7:
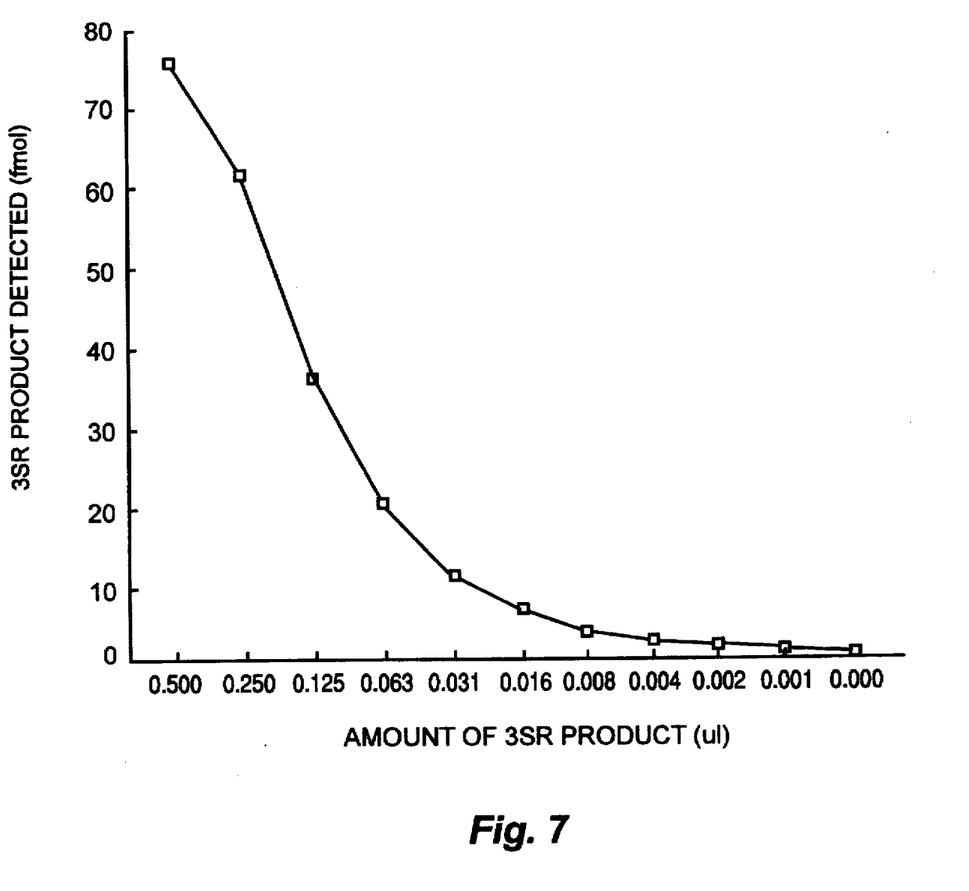
FIG. 7 depicts the detection of 3SR RNA product by bead-based sandwich hybridization (BBSH), showing a sensitivity of 1 fmol. $^{32}$P-labeled oligonucleotide 90-422 was used to detect 3SR amplified RNA by capturing it on a Trisacryl solid support using a covalently bound oligonucleotide 86-273.

Aliquots of the 3SR RNA solution were also assayed with a bead-based sandwich hybridization system (BBSH). This experiment was performed to compare the sensitivity of BBSH assay with the sensitivity of the transient state polarized fluorescence assay described, for example, in Examples 9 and 10. A Trisacryl resin-bound 30-mer oligonucleotide, 86-273 (Fahy et al., "Design and synthesis of polyacrylamide-based oligonucleotide supports for use in nucleic acid diagnostics, *Nucleic Acids Research*, 1993, in press), complementary to the 3SR generated RNA, was used as the capture sequence and $^{32}P$ labeled 90-422 oligonucleotide which is complementary to another region of the 3SR product was used as the detection probe. The Trisacryl-oligonucleotide beads and the detection oligonucleotide were used in a hybridization reaction with the 3SR RNA target at 42° C. for 60 to 90 min. Excess probe was washed away and the radioactivity associated with the solid support was used to estimate the amount of hybridized target. As shown in FIG. 7, the limit of sensitivity with the BBSH method was approximately 1 fmol (0.001 μL) of the target RNA solution. As shown in FIG. 4, and described in Examples 9 and 10, the sensitivity of the transient state polarized fluorescence assay is comparable, i.e., 1-2 fmol.

EXAMPLE 12

Thermal Stability

Figure 8:
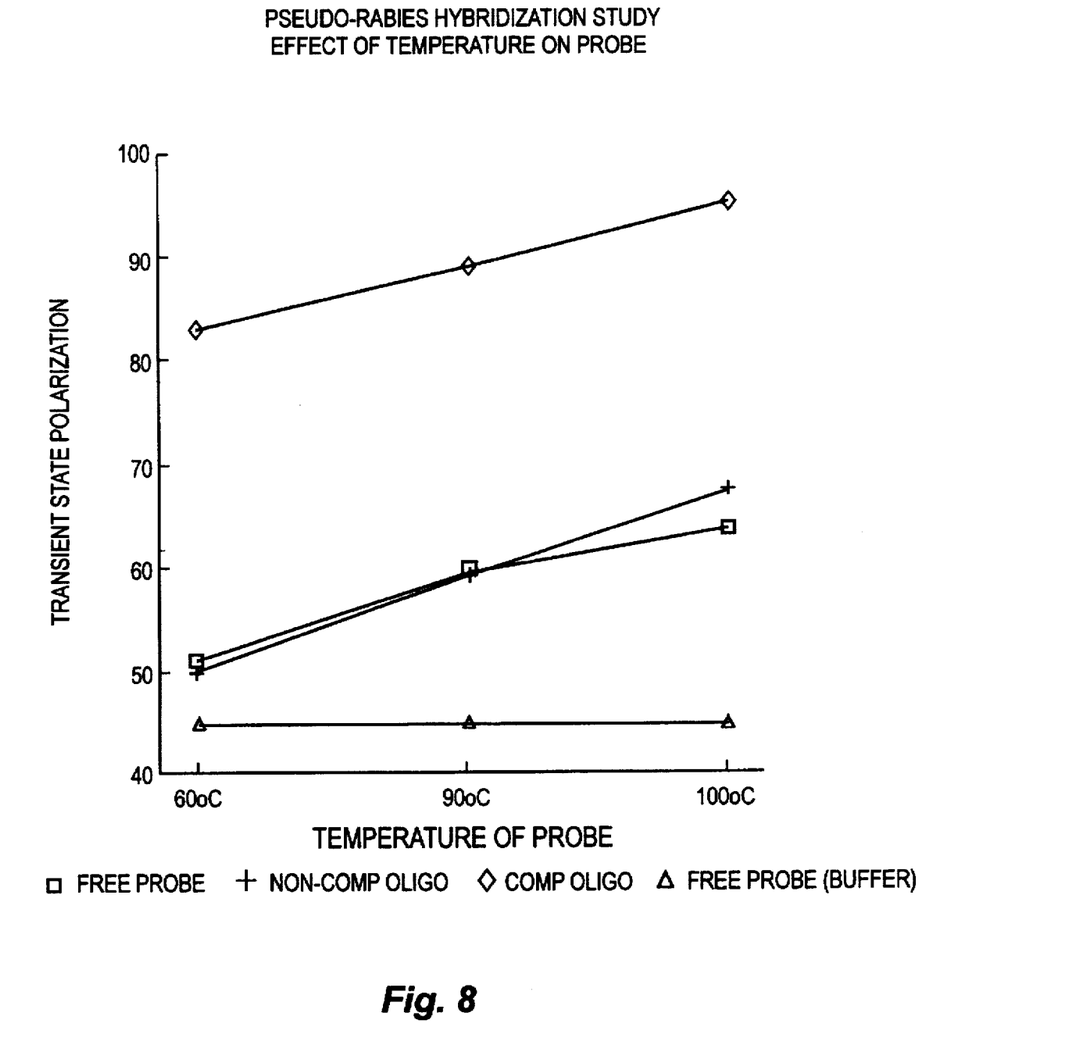
FIG. 8 depicts the effect of temperature on the detection of 3SR RNA probes.

In some amplification methods such as PCR and other applications, there is a requirement for DNA melting temperatures as high as 100° C. Accordingly, thermal stability of the caged dicarboxy silicon phthalocyanine dye was investigated using a pseudo-rabies nucleotide. A probe, complementary to a segment of pseudo-rabies DNA, was prepared using the NHS-ester of caged dicarboxy silicon phthalocyanine dye. As can be seen from FIG. 8, no decrease in probe reactivity was seen, even at 100° C. for 10 minutes.

EXAMPLE 13

Optimization of Hybridization Conditions

Preliminary experiments indicated that the conjugate was non-specifically adhering to the surface of the glass cuvettes. Initially, this problem was alleviated by using the 3SR reaction solution as the hybridization medium and this approach was effective in maintaining the conjugate in solution at sub-femtomole concentrations (data not shown). Subsequently, the conjugate was dissolved in 0.05% Tween-20/0.1% PEG-2000 and then hybridized in 5×SSP/10% dextran sulfate. Prior to carrying out the studies described in Examples 9–11, it was found that the change in fluorescence polarization of the probe upon binding to the nucleic acid targets was dependent on the temperature of the hybridization reaction (data not shown). Subsequently, temperature optima of 45° and 60° C. were determined for duplex formation with oligonucleotide DNA and 3SR RNA, respectively.

To assist in understanding the invention, the results of a series of experiments have been provided. The above examples relating to the present invention should not, of course, be construed as limiting the scope of the invention. Such variations of the invention, now known or later developed, which would fall within the purview of those skilled in the art are to be considered as falling within the scope of the invention as hereinafter claimed.

While the above examples utilize the caged dicarboxy silicon phthalocyanine, those in the art will realize that similar hybridization studies can be performed with other compositions characterized by having an oligonucleotide linked to a detectably labelled marker component which comprises a fluorophore moiety comprising a luminescent substantially planar molecular structure coupled to two solubilizing polyoxyhydrocarbyl moieties, one located on either side of the planar molecular structure.

We claim:

1. A method for preparing a marker component-conjugated oligonucleotide comprising the steps of:

a) reacting an oligonucleotide having an attached linker terminating in an amino group with an N-hydroxysuccinimide ester or in an imidazolide of a marker component a composition comprising an oligonucleotide linked to a detectably labeled marker component which comprises a fluorophore moiety comprising a luminescent substantially planar molecular structure coupled to two solubilizing polyoxyhydrocarbyl moieties, one located on either side of the planar molecular structure, to form a conjugate wherein said solubilizing polyoxyhydrocarbyl moieties are selected from a polyether, a polyol, or a water soluble polymer, and wherein said fluorophore moiety is a porphyrin derivative or an azaporphyrin derivative wherein one or more bridging carbon atoms has been replaced by nitrogen; and b) separating the conjugate formed in step (a) from unreacted oligonucleotide and from unreacted marker component.

2. A method for preparing a dye-conjugated oligonucleotide comprising the steps of:

a) reacting an oligonucleotide having an attached linker terminating in an amino group with an N-hydroxysuccinimide ester or with an imidazolide of the dye shown in FIG. 1, to form a conjugate; and b) separating the conjugate formed in step (a) from unreacted oligonucleotide and from unreacted dye.

3. The method of claim 1 or 2 further comprising performing before step (a), the step of: attaching to an oligonucleotide a linker terminating in an amino group.

4. A method for preparing marker component-conjugated oligonucleotide comprising the steps of:

a) reacting a marker component a composition comprising an oligonucleotide linked to a detectably labeled marker component which comprises a fluorophore moiety comprising a luminescent substantially planar molecular structure coupled to two solubilizing polyoxyhydrocarbyl moieties, one located on either side of the planar molecular structure, with a carbodiimide in the presence of hydrobenzotriole and in the presence of an oligonucleotide, to form a conjugate wherein said solubilizing polyoxyhydrocarbyl moieties are selected from a polyether, a polyol, or a water soluble polymer, and wherein said fluorophore moiety is a porphyrin derivative or an azaporphyrin derivative wherein one or more bridging carbon atoms has been replaced by nitrogen; and b) separating the resulting conjugate formed in step (a) from other components of the reaction mixture.

5. A method for preparing dye-conjugated oligonucleotide comprising the steps of:

a) reacting the dye having the structure depicted in FIG. 1 with a carbodiimide in the presence of hydroxybenzotriazole and in the presence of an oligonucleotide having an amino linker to form a conjugate wherein said solubilizing polyoxyhydrocarbyl moieties are selected from a polyether, a polyol, or a water soluble polymer, and wherein said fluorophore moiety is a porphyrin derivative or an azaporphyrin derivative wherein one or more bridging carbon atoms has been replaced by nitrogen; and b) separating the resulting conjugate formed in step (a) from other components of the reaction mixture.

6. A method for determining the presence or amount of a target nucleic acid sequence in a sample comprising the steps of:

a) contacting sample nucleic acid with oligonucleotide-caged dicarboxy silicon phthalocyanine dye conjugate of FIG. 2 hybridizing with said target nucleic acid sequence in homogenous solution; and b) detecting the presence or amount of such hybridization by transient state polarized fluorescence.

7. A method for determining the presence or amount of a target nucleic acid sequence in a sample comprising the steps of:

a) contacting sample nucleic acid with a composition of claim 1 wherein said composition is hybridizing with said target nucleic acid sequence in homogenous solution; and b) detecting the presence or amount of such hybridization by transient state polarized fluorescence.

8. A method for determination of the presence or amount of a target nucleic acid sequence in a sample comprising the steps of:

a) contacting a sample suspected of containing a target nucleic acid sequence with a complementary oligonucleotide hybridizing with said target sequence;

b) contacting said sample with an oligonucleotide-caged dicarboxy silicon phthalocyanine dye conjugate of FIG. 2 hybridizing to said complementary oligonucleotide; and c) detecting the presence or measuring the amount of hybridization of said conjugate with said complementary oligonucleotide.

9. A method for detection of a target nucleic acid sequence in a sample comprising the steps of:

a) contacting a sample suspected of containing a target nucleic acid sequence with a complementary oligonucleotide hybridizing with said target sequence;

b) contacting said sample with a composition of claim 1 wherein said composition is hybridizing to said complementary oligonucleotide or polynucleotide; and c) detecting the presence or measuring the amount of hybridization of said conjugate with said complementary oligonucleotide or polynucleotide.

10. A method according to either one of claims 6–9 wherein said target nucleic acid sequence is a product of nucleic acid amplification.

11. A method according to either one of claims 6–9 wherein said target nucleic acid sequence is DNA.

12. A method according to either one of claims 6–9 wherein said target nucleic acid sequence is RNA.

13. A method according to either one of claims 6–9 wherein said nucleic acid amplification is performed by polymerase chain reaction (PCR).

14. A method according to either one of claims 6–9 wherein said nucleic acid amplification is performed by ligand chain reaction (LCR).

15. A method according to either one of claims 6–9 wherein said nucleic acid amplification is performed by self-sustained sequence replication (3SR).

16. A method according to either one of claims 6–9 wherein said nucleic acid amplification is performed by transcription-based amplification system (TAS).

17. An improved nucleic acid amplification process, wherein the improvement comprising employing as a label a fluorescent probe which comprises a detectably labeled marker component which comprises a fluorophore moiety comprising a luminescent substantially planar molecular structure coupled to two solubilizing polyoxyhydrocarbyl moieties, one located on either side of the planar molecular structure wherein said solubilizing polyoxyhydrocarbyl moieties are selected from a polyether, a polyol, or a water soluble polymer, and wherein said fluorophore moiety is a porphyrin derivative or an azaporphyrin derivative wherein one or more bridging carbon atoms has been replaced by nitrogen.

18. An improved nucleic acid amplification hybridization process, wherein the improvement comprising employing as a label a fluorescent probe which comprises a detectably labeled marker component which comprises a fluorophore moiety comprising a luminescent substantially planar molecular structure coupled to two solubilizing polyoxyhydrocarbyl moieties, one located on either side of the planar molecular structure wherein said solubilizing polyoxyhydrocarbyl moieties are selected from a polyether, a polyol, or a water soluble polymer, and wherein said fluorophore moiety is a porphyrin derivative or an azaporphyrin derivative wherein one or more bridging carbon atoms has been replaced by nitrogen.

* * * * *